United States Patent
Falck et al.

(10) Patent No.: US 6,179,779 B1
(45) Date of Patent: Jan. 30, 2001

(54) REPLACEABLE PRISM SYSTEM FOR APPLANATION TONOMETER

(75) Inventors: Francis Y. Falck, Stonington; Robert W. Falck, Pawcatuck, both of CT (US)

(73) Assignee: FFHK Development Company LLC, Mystic, CT (US)

(*) Notice: Under 35 U.S.C. 154(b), the term of this patent shall be extended for 0 days.

(21) Appl. No.: 08/995,794

(22) Filed: Dec. 22, 1997

(51) Int. Cl.⁷ ........................................ A61B 3/16
(52) U.S. Cl. ................. 600/398; 600/399; 600/400; 600/405; 600/406
(58) Field of Search ............... 600/398, 399, 600/400, 405, 406; 73/82; 351/212, 213

(56) References Cited

U.S. PATENT DOCUMENTS

| 5,070,875 | 12/1991 | Falck et al. |
| 5,190,042 | 3/1993 | Hock . |
| 5,203,331 | 4/1993 | Draeger . |
| 5,634,458 | 6/1997 | Joshi et al. |

FOREIGN PATENT DOCUMENTS

| 2643879 | 3/1978 | (DE) . |
| 0418746 | 3/1991 | (EP) . |
| 2295226 | 5/1996 | (GB) . |
| 116633 | 12/1957 | (SU) . |

Primary Examiner—Linda C. M. Dvorak
Assistant Examiner—R. Kearney
(74) Attorney, Agent, or Firm—Eugene Stephens & Associates

(57) ABSTRACT

An applanation tonometer with a replaceable prism for contacting a cornea has emitter and detector ports arranged opposite each other on opposite sides of a longitudinal axis, with the ports aimed at about 45° to the longitudinal axis. Light from an emitter then passes through the emitter port and crosses the prism axis to be incident and reflected from an emitter-reflecting surface of the prism and become incident on the applanation surface. Light reflected from the applanation surface is incident on and reflected from a detector-reflecting surface opposite and parallel with the emitter-reflecting surface to proceed across the prism axis to the detector port. Such an arrangement produces reliable applanation signals and varies the spacial intensity of light reflected from the applanation surface so that the tonometer can automatically distinguish between concentric and eccentric contact of the applanation surface with a cornea.

30 Claims, 7 Drawing Sheets

REPLACEABLE PRISM SYSTEM FOR APPLANATION TONOMETER

TECHNICAL FIELD

Applanation tonometers.

BACKGROUND

This invention improves on the tonometer of U.S. Pat. No. 5,070,875, the disclosure of which is hereby incorporated by reference. The '875 patent discloses an applanation tonometer having a replaceable prism; and this invention improves on the prism and its replacement, while otherwise relying on tonometer components such as described in the '875 patent.

Prisms for applanation tonometers have proved to be problematic. The art has suggested several prism variations for applanation tonometers, including U.S. Pat. Nos. 5,190,042 and 5,203,331. None of these have yet demonstrated operability sufficient to be successful in the marketplace. The problems involve reliable production of an accurate applanation signal and the difficulty of combining this with a tonometer having a conveniently replaceable prism producing reliable operation at a low cost.

SUMMARY OF THE INVENTION

The improved prism for our tonometer solves these problems partly by arranging emitter and detector ports opposite each other on opposite sides of a longitudinal axis so that axes of the emitter and detector ports are angled about 45° to the longitudinal axis. This makes the light-transmitting surfaces of the emitter and detector ports approximately perpendicular to each other. Internal-reflecting prism surfaces for the emitter and detector are also arranged opposite each other on opposite sides of the longitudinal axis and proximate to the applanation surface. This makes the emitter- and detector-reflecting surfaces approximately parallel to each other. A light path proceeding from a source through the emitter port is angled at about 45° to the longitudinal axis and directed across the longitudinal axis for incidence on the emitter-reflecting surface. From there, the light is incident on an applanation surface, and a portion of the light reflected from the applanation surface is incident on the detector-reflecting surface. A light path to the detector port for the light reflected from the applanation surface and the detector-reflecting surface proceeds at an angle of about 45° to the longitudinal prism axis across the longitudinal axis and is output at the detector port.

With a prism of such a configuration receiving light from a light-emitting diode, which is presently preferred as a source of prism illumination, the light incident on the applanation surface can be made to vary in intensity radially from a center of the applanation surface to a perimeter of the applanation surface. A consequence of such a varying light distribution at the applanation surface is that the amount of reflected light reaching the detector upon concentric contact of the applanation surface with a cornea differs distinguishably from an amount of reflected light reaching the detector upon eccentric contact of the applanation surface with a cornea. The readily distinguishable difference in detected light from concentric and eccentric contact with a cornea is preferably used to determine that the prism is properly positioned to proceed with an intraocular pressure measurement sequence.

A prism having desirable light-transmitting characteristics is also preferably replaceable and disposable. This is accomplished by provisions for easy insertion and withdrawal of the prism, making the prism inexpensive, providing a system for requiring and detecting replacement of the prism, and making the tonometer quickly and reliably calibrated to each new prism. We also prefer making the tonometer responsive to input for adjusting an intraocular pressure measurement to accommodate variations in corneal curvature and thickness of a particular eye being examined.

DRAWINGS

Figure 9:
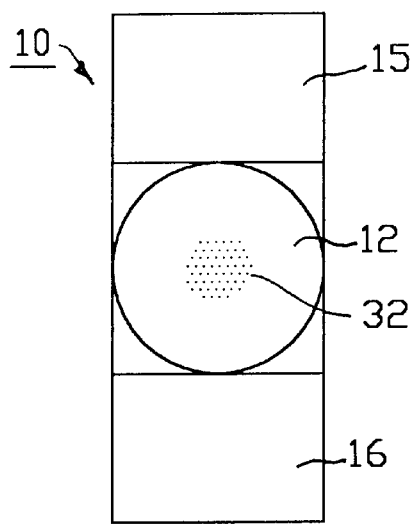
Figure 10:
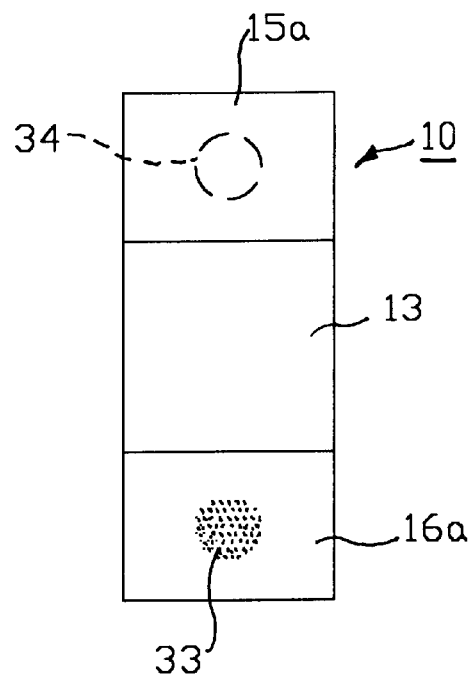

FIGS. 9 and 10 schematically show respective front and rear views of alternative preferred embodiments of prism 10 illustrating ways of varying the intensity of light distribution to ensure that an applanation surface concentrically contacts a cornea for each pressure measurement that is undertaken.

Figure 11:
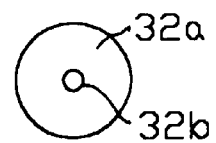

FIG. 11 schematically shows an alternative preferred embodiment of a way of affecting light distribution for automatically requiring centering of the applanation surface with a cornea.

DETAILED DESCRIPTION

Infrared light-emitting diodes that are preferred for illuminating applanation tonometers are not point sources. Also, within the compact confines of an applanation tonometer, it is not practically possible to collimate light from LED sources. The light from these sources thus diverges and spreads through a prism, making it difficult to consistently produce a reliable applanation signal with the minor amount of the total light that reaches a detector.

It is also possible for a tonometer light source to be a laser outputting collimated light that does not diverge as much as light from an LED source. The preferred radiation for use in a tonometer is infrared; and laser sources are available for producing collimated infrared radiation, which has several advantages for illuminating a tonometer prism.

We have found signal generation to be especially problematic when light paths within the tonometer prism are approximately parallel with each other so as to interfere with each other. Our preferred solution to all these problems is best shown by the prism 10 that is schematically illustrated in the drawings.

Figure 1:
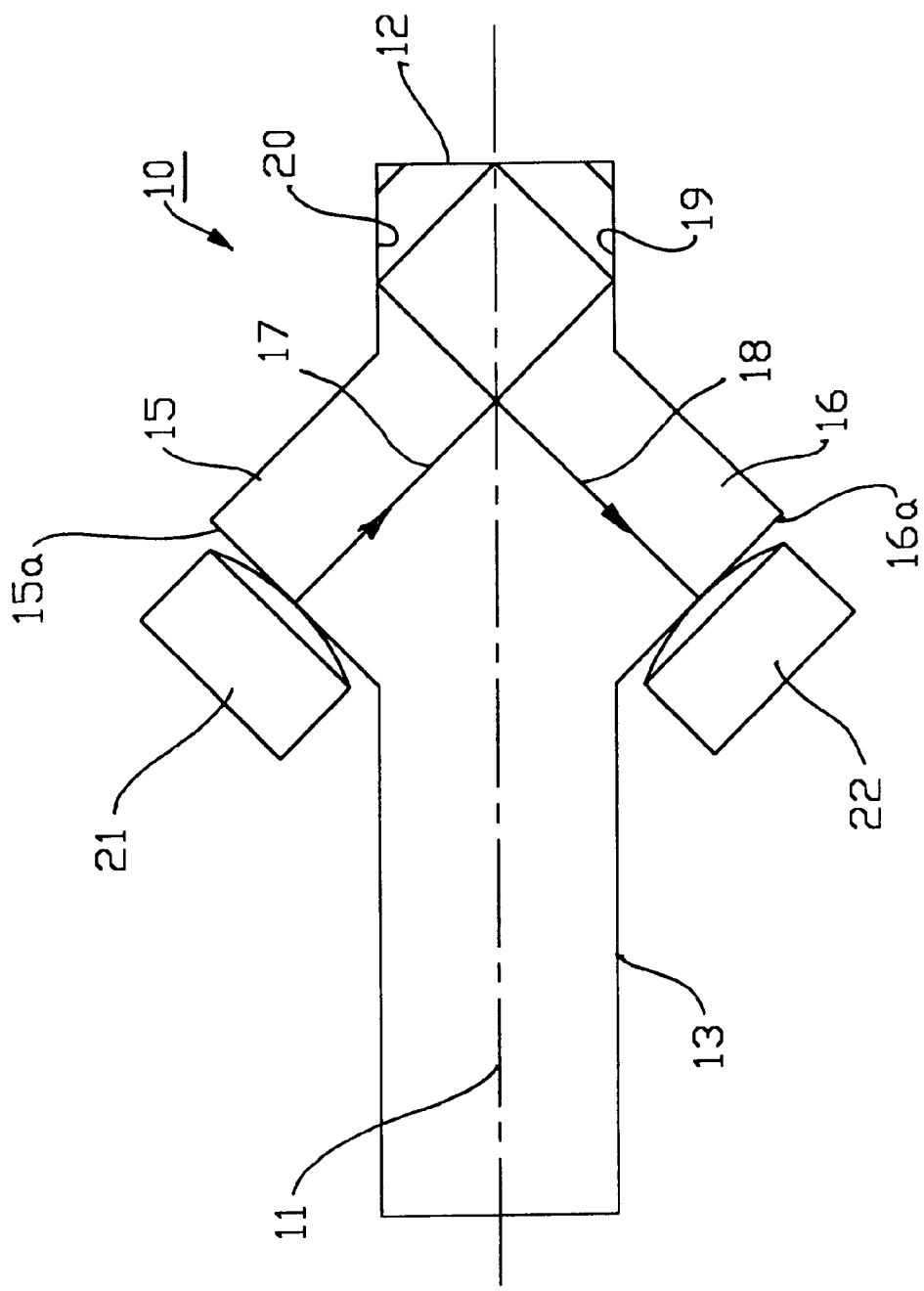
FIG. 1 is a schematic plan view of a preferred embodiment of replaceable prism positioned relative to an emitter and detector of a tonometer.
Figure 2:
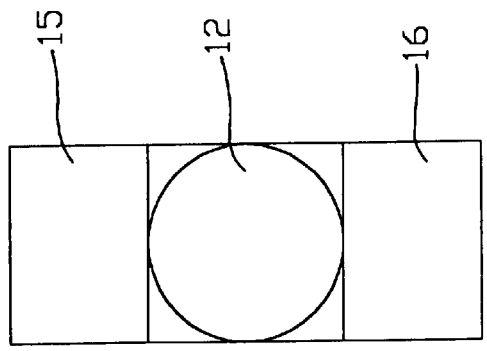
FIG. 2 is a schematic front elevational view of the prism of FIG. 1.
Figure 3:
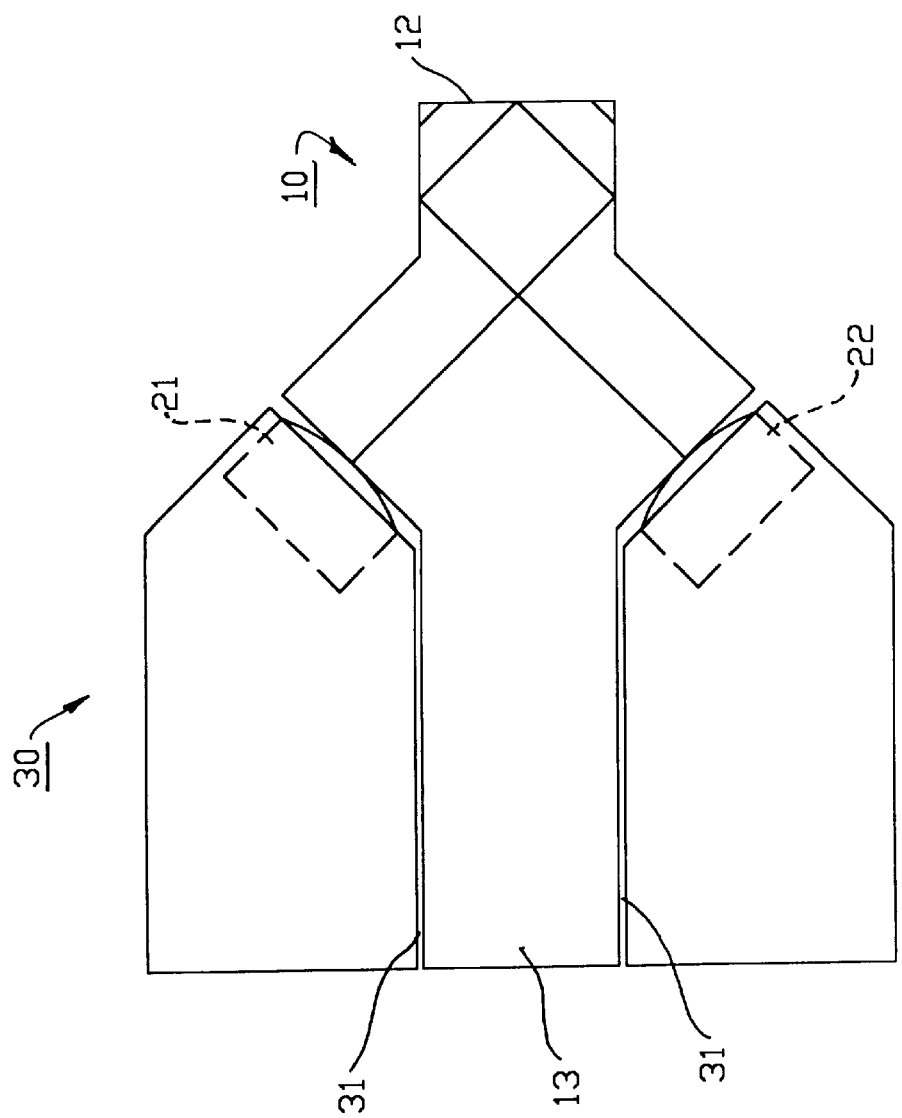
FIG. 3 is a schematic plan view of the prism of FIG. 1 replaceably positioned in a prism holder.

Prism 10 has a longitudinal axis 11 centered on a preferably circular applanation surface 12 and providing a viewing axis for a tonometer operator. A viewing arm 13 of prism 10 is removably insertable into a prism holder 30, as shown in FIG. 3, so that prism 10 is readily replaceable.

Prism 10 has an emitter port 15 and a detector port 16 arranged opposite each other on opposite sides of longitudinal axis 11. Emitter and detector ports 15 and 16 are each angled about 45° to longitudinal axis 11 so that light paths from and to emitter and detector ports are also angled at preferably 45° to longitudinal axis 11. Interface surfaces 15a and 16a respectively for emitter and detector ports 15 and 16 are disposed approximately perpendicular to each other. A light path 17 from emitter port 15 crosses longitudinal axis 11 approximately perpendicular to a light path 18 directed toward detector port 16, to avoid any interference between beams, which are never nearly parallel with each other within the prism.

Prism 10 has an internally reflecting emitter surface 19 for emitter light traveling along path 17 and an internally reflecting detector surface 20 directing light along detector path 18. Prism surfaces 19 and 20 are disposed opposite each other on opposite sides of longitudinal axis 11 and are preferably parallel with each other. Light from an emitter 21 proceeds along path 17 to be incident on and reflected by emitter-reflecting surface 19 and become incident on applanation surface 12. Light that is internally reflected from applanation surface 12 is incident upon detector-reflecting surface 20, which directs such reflected light along path 18 toward detector 22.

Prism 10 is preferably molded of optical quality resin material so that it can be disposed of after each use with minimal expense. Prism disposal after use is important to avoid transmitting infectious agents from one person to another. Prions, for example, have been found in the tears of infected people, which raises the possibility that infectious disease can be transmitted from one person to another via tear contact. It is also not possible to sterilize an object contaminated with prions, so the only safe recourse is to make prism 10 disposable. To make this feasible, our prism 10 has a simple moldable shape and is configured to be conveniently slipped in and out of a held position by means of its viewing arm 13. Also contributing to replacement convenience is the fact that emitter port 15 and detector port 16 are identical and are interchangeable. This allows prism 10 to be inserted into a tonometer in either of two workable positions disposing interface surfaces 15a and 16a, respectively, against either an emitter or a detector. For light transmission purposes, we prefer that surfaces 15a and 16a of prism 10 contact surfaces of emitter 21 and detector 22 without leaving an air gap.

We have found from experiments with many other prism configurations that the arrangement of emitter and detector ports and light paths as shown for prism 10 is significantly better at producing a reliable applanation signal. Light that diverges too far from the illustrated paths is diverted by prism 10 from detector 22, either by external loss from transmitting out of prism 10 or by being internally reflected away from detector port 16. The light paths shown in prism 10 also avoid parallel courses tending to produce interference. The advantages of the illustrated light paths are especially clear for emitters 21 using LED sources, but the illustrated paths also work well with laser emitters 21. The illustrated configuration of prism 10 also produces an optimum distribution of light intensity at applanation surface 12, as explained below.

Prism holder 30 is also preferably molded of resin material and configured to receive the viewing arm 13 of prism 10 and to hold and support emitter 21 and detector 22. Prism viewing arm 13 preferably has a sliding fit in holder recess 31. Otherwise, holder 30 can be configured in many ways to accommodate the needs of a tonometer, including electric leads for emitter 21 and detector 22 and the necessary retention and support for prism 10, emitter 21, and detector 22.

Figure 6:
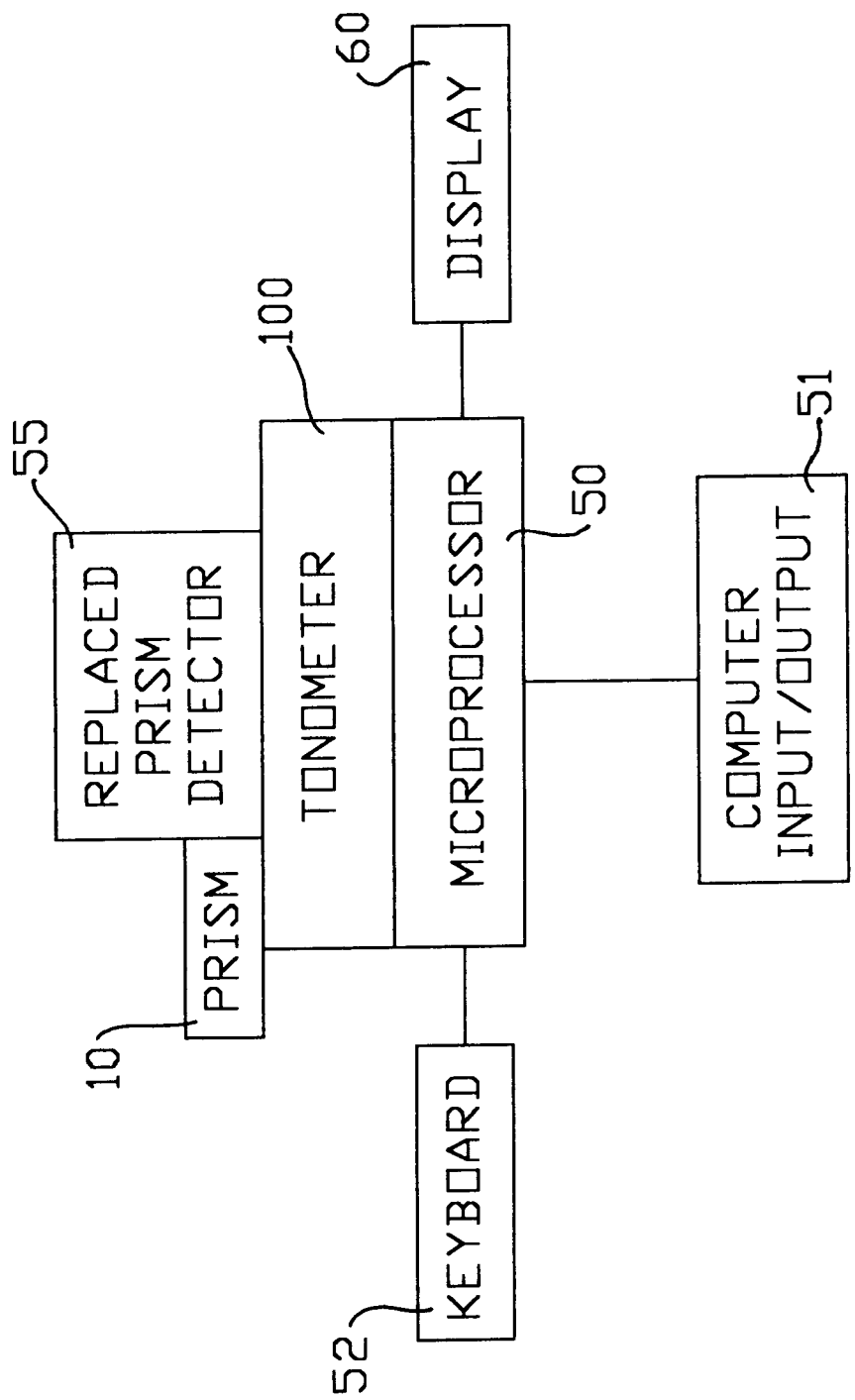
FIG. 6 is a schematic diagram of a preferred embodiment of a replaceable prism tonometer having a replaced prism detector.

Several factors can vary a signal intensity at detector 22. These include the power of a battery supplying energy to emitter 21, slight variations in replaceable prisms 10, and slight differences in the seating of a prism 10 in holder 30. Because of such variables, it is important to calibrate tonometer 100 before each intraocular pressure-measuring sequence. This is preferably accomplished with microprocessor 50 that is schematically illustrated in FIG. 6 as part of tonometer 100.

Figure 5:
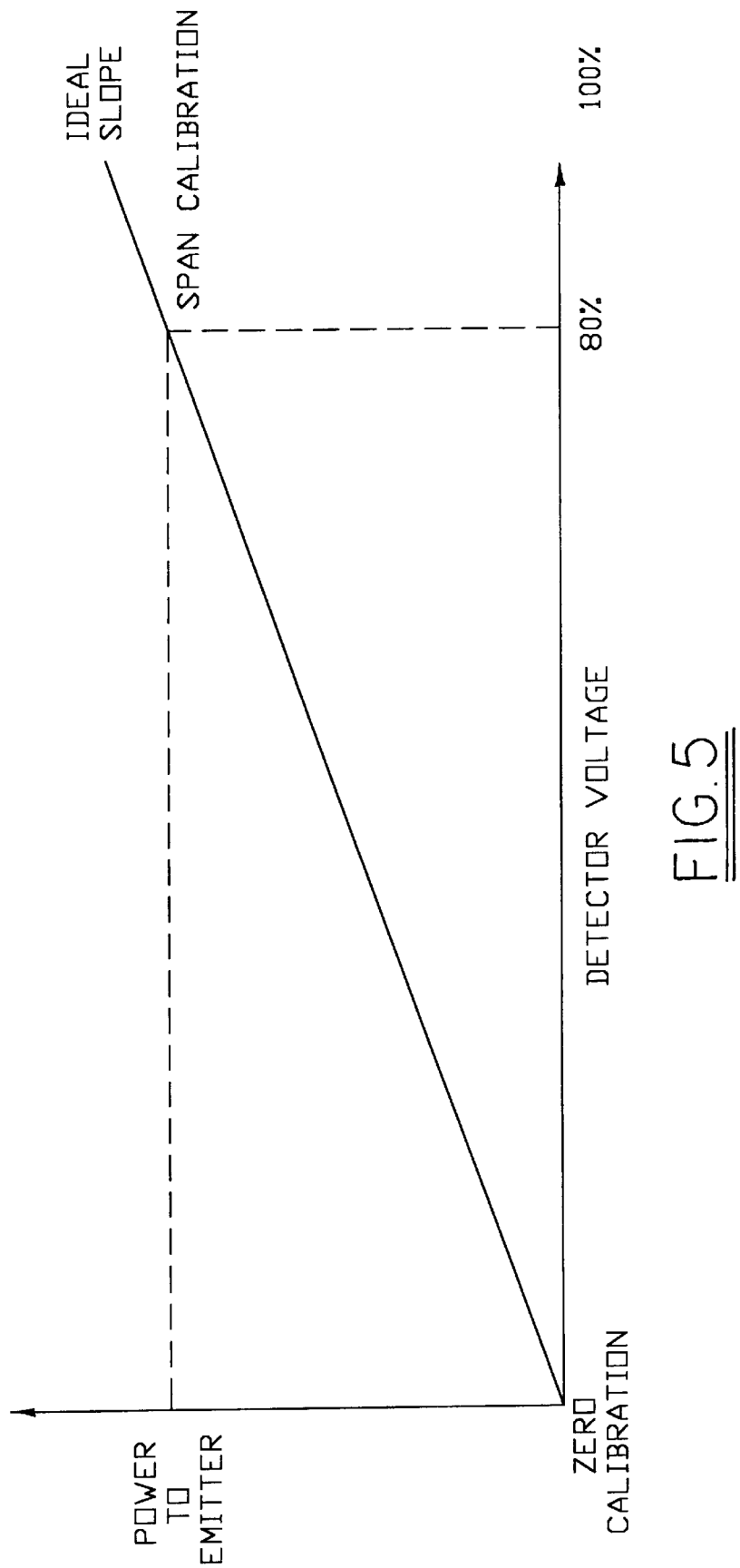
FIG. 5 is a graph of a preferred embodiment of a replaceable prism tonometer calibration system.

Our preferred calibration, as shown in FIG. 5, first energizes emitter 21 to full power while applanation surface 12 contacts only air so that full reflection from applanation surface 12 proceeds toward detector 22. This establishes an offset value in the form of an amount of signal produced by detector 22 upon full illumination. Then a slope and a span calibration value is established by reducing the energy to the emitter to produce a predetermined detector output value departing from the offset value. We prefer that power to the emitter be reduced sufficiently to bring the detector signal to 80% of its offset or full illumination value, but other predetermined values can also be used to produce different slopes. Once the offset or full illumination value of the detector signal is known, along with the emitter power needed to bring the detector signal to the predetermined slope value of 80%, for example, then these values can be used for calibrating applanation signals. The relationship can be expressed as:

$$MV = \frac{(DS - CV) \cdot SC}{S - CV}$$

where: S, the slope, is a predetermined percentage of the detector signal, such as 80% as preferred in the illustration;

SC, the span calibration value, is the power required to energize the emitter to produce the predetermined detector signal;

CV, the zero calibration value, is the detector signal resulting from full power applied to the emitter;

DS, the raw detector signal, is produced upon applanating contact of the prism with a cornea; and MV is the measured applanation value.

Each measurement signal is then automatically processed by microprocessor 50 according to the calibration, and the calibration values are preferably established each time a new prism is inserted into the tonometer. This ensures that all pressure measurements are properly processed by the calibration criteria and that improperly calibrated measurements are avoided. The calibration procedure also occurs at least as fast as a user can become ready to perform a measurement.

Figure 4:
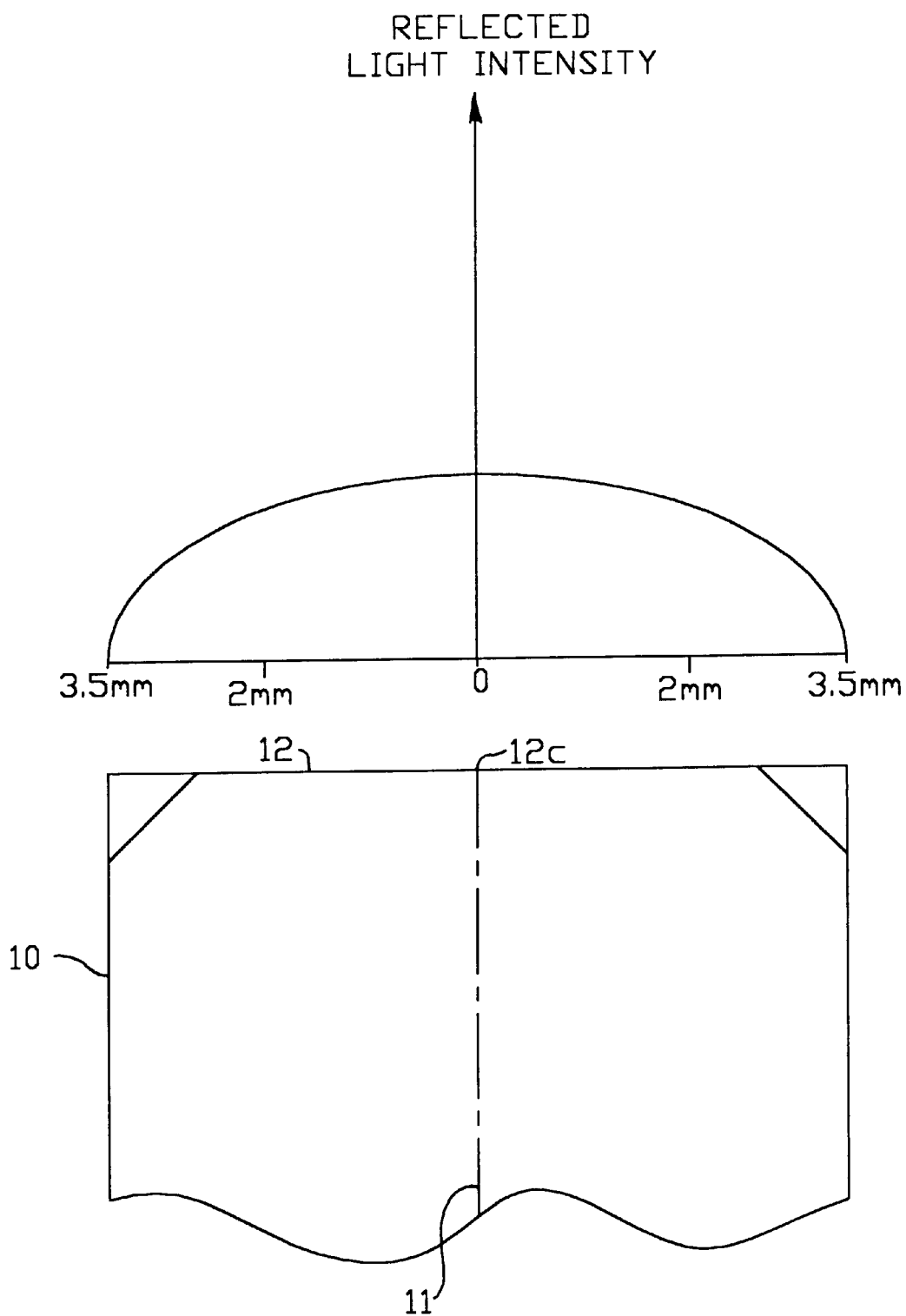
FIG. 4 is a schematic graph of light intensity distribution on the applanation surface of the prism of FIGS. 1–3.

The optical arrangement of emitter 21, detector 22, and prism 10 providing internal pathways for light from an LED source is also preferred for varying a spacial distribution of light intensity incident on applanation surface 12. When substantially all of the light incident on applanation surface 12 is reflected toward detector 22, a preferred variation in intensity distribution of the reflected light when surface 12 is in contact only with air is illustrated in FIG. 4, which shows that the spacial intensity of the reflected light is maximum at a center of applanation surface 12 coinciding with longitudinal axis 11 of prism 10. The reflected light intensity curve is preferably dome-shaped as illustrated with light intensity remaining fairly high within a 2 mm radius of a center 12c of applanation surface 12. Outside a 4 mm central diameter, reflected light intensity falls off rapidly toward zero at the outer perimeter of applanation surface 12, which preferably has a 7 mm diameter. Alternative preferred variations in spacial distribution of reflected light intensity from applanation surface 12 are also possible and are described relative to FIGS. 9–11.

Positioning the emitter and detector at equal distances from applanation surface 12 helps establish the preferred reflected light intensity profile. Keeping the emitter and detector at optimum distances from their respective reflector surfaces 19 and 20 also contributes, and we have found by experimentation that this optimum distance is preferably about 11 to 15 mm. Shorter distances tend to produce a more sharply peaked reflected light intensity profile, and longer distances tend to produce a flatter profile for a lesser total of reflected light.

The illustrated spacial distribution of reflected light intensity is preferred for ensuring that applanation surface 12 concentrically contacts a cornea before any intraocular pressure-measuring sequence begins. As applanation surface 12 contacts a cornea, the surface tension of tears on the cornea forms a meniscus around a slight applanation of the cornea from the surface tension effect. The diameter of a minimum contact meniscus is difficult to measure but is approximately 1.5 to 2 mm. If applanation surface 12 contacts a cornea concentrically so that longitudinal axis 11 and applanation surface center 12c contact a center of the cornea, the light incident on applanation surface 12 passes into the eye throughout the 1.5 to 2 mm diameter within the meniscus from contact only. If this contact is concentric with the cornea, the light reflected back to detector 12 is reduced by a maximum amount, because the light lost by transmission through applanation surface 12 occurs in the highest intensity central region of the graph shown in FIG. 4. Conversely, if applanation surface 12 contacts a cornea eccentrically, the contact meniscus will be offset toward a lower intensity region of the dome configuration of the light intensity at surface 12, and the light reflected back to detector 22 will be reduced by a lesser amount. Microprocessor 50 is preferably programmed to distinguish between maximum reduction in reflected light upon concentric contact with a cornea, compared with a lesser reduction in reflected light on eccentric contact with a cornea.

In effect, if a user guiding prism 10 into contact with a cornea misses slightly and achieves eccentric contact, microprocessor 50 determines this and gives the user an indication, preferably via display 60, without proceeding with an intraocular pressure-measuring sequence. The user can then try again for concentric contact, which is automatically detected and confirmed so that the tonometer automatically proceeds with an intraocular pressure-measuring sequence. Concentric corneal contact is important for accuracy of intraocular pressure measurement readings, and concentricity is preferably held within about 1.0 to 1.5 mm. A reason for this is that a cornea is dome-shaped and stiffer around its edges than at its center. This leads to inaccurate readings from the increased stiffness of the cornea to eccentric applanation. For tonometer 100 to automatically require concentric applanation of a cornea with prism surface 12 ensures that inaccurate readings from eccentric corneal contact are avoided.

There are other preferred ways of varying the light intensity distribution reaching detector 22 to ensure automatic concentricity of applanation before undertaking an intraocular pressure measurement. One such alternative is to divert, eliminate, or otherwise block light from a central region of applanation surface 12 from reaching detector 22. The central lightless region of applanation surface 12 is then made approximately the size of a region of minimum contact of prism 10 with a cornea. If such contact is concentric, then a minimum change in reflected light reaching detector 22 will occur; and if such contact is eccentric, a larger change in reflected light reaching detector 22 will occur. The difference between concentric and eccentric contact will again be detectable by different amounts of light reaching detector 22 so that a pressure measurement sequence can proceed, depending on whether detected contact is concentric or eccentric.

A few of the many ways of accomplishing this sort of automatic concentricity determination are schematically illustrated in FIGS. 9–11. One preferred way, as illustrated in FIG. 9, is to make a central region 32 of applanation surface 12 substantially transmissive of internally incident light when applanation surface 12 is in contact only with air. This can be done by leaving central surface region 32 unpolished or deliberately roughened to diffuse incident light. A suitable coating applied in central region 32 could have a similar effect of transmitting outside of prism 10 all or most of the radiation internally incident on central region 32. Then, concentric contact of applanation surface 12 with a cornea will substantially coincide with the area of central region 32 and have little effect on light internally reflected to detector 22. Some change in internally reflected light is desirable so that detector 22 can determine that corneal contact has been made, but a change in the amount of reflected light upon corneal contact can be made minimal. This can be done by making central area 32 slightly smaller than a minimum corneal contact area or by making central region 32 reflect a minor portion of incident light when in contact with air and transmit all incident light when in contact with a cornea.

With any such arrangement, viewed from detector 22, a slight change in reflected light would indicate concentric corneal contact, and a larger change in reflected light would indicate eccentric corneal contact. The larger change occurs because an eccentric corneal contact blocks reflection of light outside of central region 32, where light reflection is otherwise more intense than from within central region 32.

Establishing a transmissive central region 32 on applanation surface 12 is preferred for automatic concentricity determination, because it locates the determining region 32 at the plane of applanation surface 12, where corneal contact occurs. Substitutes for this may be possible, however, as schematically suggested in FIG. 10. An opaque spot 33 can be formed on detector port surface 16a to block from detector 22 light reflected from a central region of applanation surface 12. Opaque spot 33 would be sized to block out light from a somewhat smaller region of applanation surface 12 than is involved in minimal corneal contact, or spot 33 could transmit only a minor portion of light from a central region of applanation surface 12. Either way, detector 22 would receive slightly less light on concentric corneal contact and significantly less light on eccentric corneal contact.

Another solution is schematically shown by broken line spot 34 on emitter port surface 15a. Spot 34 is positioned to block light from reaching a central region of applanation surface 12 and is sized or made partially transmissive to produce a minor reduction in reflected light upon concentric contact so that a larger reduction in reflected light indicates eccentric contact.

Another of many possible alternatives for shapes of central regions 32 on applanation surface 12 is shown in FIG. 11 as a transmissive circle 32a having a tiny reflective center 32b. The diameter of circle 32a is preferably about 1.5 to about 2 mm, to match the size of an area of minimum contact between applanation surface 12 and a cornea. Reflective central spot 32b then allows detector 22 to determine that contact has been made by slightly reducing reflected light, while any larger reduction in reflected light indicates that such contact is eccentric.

Collimated light from a laser emitter 21 can produce varied spacial intensity in light reflected from applanation surface 12 by using the alternatives of FIGS. 9–11. Although laser light would tend to be more uniformly distributed on applanation surface 12, it is also less diffuse so that blocking or filtering a central zone of a laser beam in any of the ways equivalent to the FIGS. 9–11 alternatives can produce a varying spacial distribution enabling detector 22 to distinguish between concentric and eccentric cornea contact.

Microprocessor 50 of tonometer 100, by any of these ways of varying spacial distribution of light intensity reaching detector 22, can determine that corneal contact has been made and is either concentric or eccentric. If contact is eccentric, a user is informed via display 60 and no measurement occurs; but if contact is concentric, tonometer 100 proceeds with a measuring sequence.

An intraocular pressure measurement sequence preferably involves several steps. These include applanating the cornea to a reference size and a measurement size that differ from each other; noting the force difference required for this; and repeating the process, preferably two more times to produce an average value. Any value differing by more than 10 percent from another value is discarded, and applanations are quickly repeated until three similar transitions from reference size to measurement size are completed. It is also possible to program microprocessor 50 to note force changes required to proceed in each direction from reference area to measurement area and from measurement area back to reference area. This can produce six values for the same brief time interval used in implementing the mechanical force changes. The three to six values are averaged to constitute a single intraocular pressure measurement reading, and the process is repeated preferably two more times to produce three readings for the eye being examined. All this happens quickly within a few seconds, whereupon the instrument displays and records a pressure measurement based on the applanation forces used for the eye that was examined. The process is then repeated in a similar way on the other eye to produce a second pressure reading. The pressure readings can be stored as well as displayed and can be transmitted to a computer 51 as shown in FIG. 6.

Studies have shown that applanation procedures for determining intraocular pressure are affected by corneal thickness and curvature. Thinner corneas are more flexible or softer than thicker ones so that thinner corneas applanate with less pressure and produce lower intraocular pressure measurement readings. Also, flatter or less domed corneas are softer than corneas shaped with a steeper dome so that flatter corneas also produce lower intraocular pressure measurement readings. Both thickness and curvature of a cornea of an eye to be examined can be measured independently with known procedures, and microprocessor 50 is preferably programmed to receive cornea thickness and curvature information via keyboard 52 or computer 51. Microprocessor 50 then applies corneal thickness and curvature information to adjust intraocular pressure measurements to appropriately corrected values. Microprocessor operation of tonometer 100 makes such an adjustment both feasible and convenient.

Making prism 10 conveniently and inexpensively replaceable allows each patient to be examined with a fresh prism to ensure that no infectious agents are transmitted from one patient to another. Our tonometer can also be configured to require that prism 10 is replaced for each new patient. For this, microprocessor 50 is preferably programmed to allow two complete intraocular pressure-measuring sequences (one for each eye of a patient) and then no longer operate until prism 10 is replaced. To accomplish this, we use a replaced prism detector 55 preferably mounted in prism holder 30 to interact with prism 10 to produce an indication that a prism has been replaced. Possible interactions between prism 10 and replaced prism detector 55 include sensing a magnetic code on a prism and erasing the code after completing two pressure-measuring sequences; sensing a frangible tab of resin or foil that enters prism holder 30 with a replaced prism to indicate prism replacement, but is broken or disabled when prism 10 is withdrawn from holder 30; and sensing a coating that changes after brief exposure to infrared light so that a sensed change in the coating indicates that the prism has been used.

Figure 7:
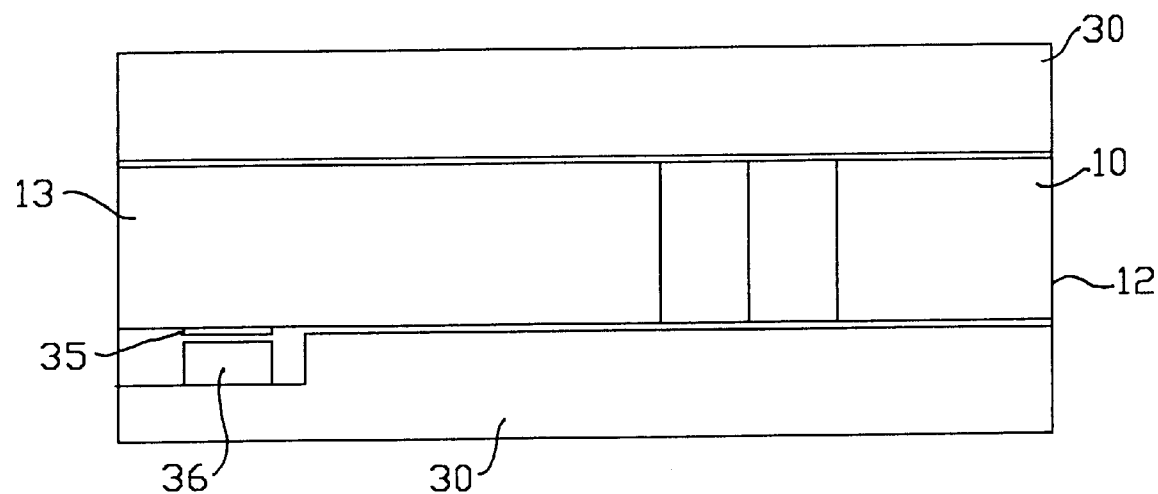
FIGS. 7 and 8 are schematic views of alternatives for replaced prism detectors.
Figure 8:
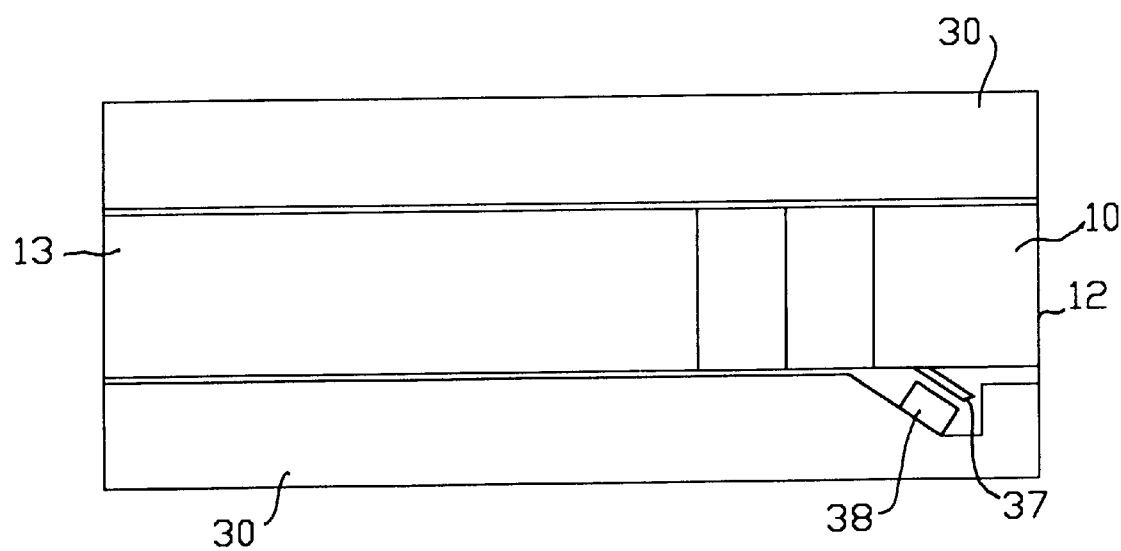

Two of these alternatives are illustrated schematically in FIGS. 7 and 8. A magnetic strip 35 mounted on prism 10 is encoded magnetically to indicate a replaced prism; and this code is read by a magnetic reader 36 arranged in holder 30, as shown in FIG. 7. After completing the permissible number of intraocular pressure measurements, reader 36 erases the code on magnetic strip 35 so that prism 10 cannot be reused.

In the embodiment of FIG. 8, a tab 37 of fragile resin or foil material is located in a region of prism 10 that receives infrared light. A detector 38 then senses the presence of tab 37 when prism 10 is illuminated and thereby confirms that prism 10 has been replaced. Tab 37 is dimensioned to be frangible so that it breaks away when prism 10 is withdrawn from holder 30 after completing a measuring sequence. Tab 37 can be molded integrally with prism 10 or applied to prism 10 by adhesive or other means. One way to ensure that tab 37 breaks away when prism 10 is withdrawn is to angle tab 37 as illustrated so that it flexes without breaking as prism 10 is inserted into holder 30, but is broken away when prism 10 is withdrawn.

Many other alternatives are possible for ensuring the necessary interaction between prism 10 and replaced prism detector 55. Again, operation of the tonometer by microprocessor 50 facilitates any desired implementation of a replaced prism detector 55.

We claim:

1. In a tonometer having an applanation prism with an applanation surface that engages a cornea of an eye being examined, an optical system including an emitter directing light into the prism to be incident on and at least partially reflected from the applanation surface and a detector detecting light reflected from the applanation surface and a microprocessor responsive to a signal from the detector representing total light reflected from the applanation surface and received by the detector, the improvement comprising:

a. the emitter, detector, and prism being arranged relative to each other so that spacial distribution of light intensity reflected from the applanation surface varies radially from a center of the applanation surface to a periphery of the applanation surface;

b. the microprocessor being programmed to determine that the signal from the detector at a predetermined non-contact value represents the radially varied light intensity reflecting from the applanation surface to the detector when the applanation surface is not in contact with the eye being examined;

c. the microprocessor being programmed to determine that the signal from the detector at a predetermined concentric contact value less than the non-contact value represents the radially varied light intensity reflecting from the applanation surface to the detector when the applanation surface concentrically contacts the cornea of the eye being examined; and d. the microprocessor being programmed to determine that the signal from the detector at an eccentric contact value less than but differing from the concentric contact value represents the radially varied light intensity reflecting from the applanation surface to the detector when the applanation surface eccentrically contacts the cornea of the eye being examined.

2. The improvement of claim 1 wherein the microprocessor is programmed to proceed with the pressure measurement in response to the signal from the detector at the concentric contact value and not to proceed with the pressure measurement in response to the signal from the detector at the eccentric contact value.

3. The improvement of claim 1 wherein the spacial distribution of light intensity reflected from the applanation surface is more intense at a center of the applanation surface and less intense at the periphery of the applanation surface.

4. The improvement of claim 3 wherein the emitter is a light-emitting diode having an area source of light.

5. The improvement of claim 1 wherein the emitter and the detector are arranged on opposite sides of an axis of the prism intersecting a center of the applanation surface.

6. The improvement of claim 1 wherein a central portion of the spacial distribution of light intensity reflected from the applanation surface does not reach the detector regardless of contact of the prism with a cornea of the eye being examined.

7. The improvement of claim 1 wherein the cenrial portion of the light reflected from the applanation surface is circular with a diameter of from about 1.0 mm to about 1.5 mm.

8. The improvement of claim 1 wherein a central region of the applanation surface is substantially transmissive to light from the emitter regardless of contact of the prism with a cornea.

9. The improvement of claim 8 wherein the central region of the applanation surface is circular with a diameter of from about 1.0 to about 1.5 mm.

10. The improvement of claim 1 wherein the spacial distribution of light intensity reflected from the applanation surface is configured to have recuced intensity in a central region of the applanation surface.

11. The improvement of claim 1 wherein the signal from the detector at the eccentric contact value is less than the signal from the detector at the concentric contact value.

12. The improvement of claim 1 wherein signal from the detector at the eccentric contact value is larger than the signal from the detector at the concentric contact value.

13. The improvement of claim 1 wherein the microprocessor is arranged for receiving input on a corneal parameter of an eye to be measured for intraocular pressure and is programmed to adjust an intraocular pressure measurement to accommodate for the corneal parameter received via input.

14. The improvement of claim 13 wherein the corneal parameter is curvature of the cornea of the eye being examined.

15. The improvement of claim 13 wherein the corneal parameter is thickness of the cornea of the eye being examined.

16. The improvement of claim 1 wherein the microprocessor is programmed to calibrate the tonometer by establishing a detector offset value for full emitter illumination and full reflection from the applanation surface and establishing a slope value applied to a detected measurement value, the slope value being a predetermined detector output value above the offset value divided by an emitter-energizing value needed to produce the predetermined detector output value.

17. The improvement of claim 1 wherein the tonometer has a prism detector for detecting the presence of the prism in the tonometer and the microprocessor is programmed to permit only a predetermined number of intraocular pressure readings with the prism placed in the tonometer, whereupon replacement of the prism is required to actuate the prism detector and allow a new set of a predetermined number of intraocular pressure readings.

18. A method of operating the tonometer of claim 1 to ensure concentric engagement of the prism with a cornea of the eye being examined, the method comprising:
  a. engaging the cornea of the eye being examined with the applanation surface of the prism;
  b. receiving an indication from the microprocessor that the prism engagement with the cornea of the eye being examined is eccentric;
  c. removing and repositioning the applanation surface of the prism into contact with the cornea of the eye being examined; and
  d. proceeding with an intraocular pressure measurement upon a determination by the microprocessor that contact between the applanation surface and the cornea of the eye being examined is concentric.

19. The improvement of claim 1 wherein the prism has a longitudinal axis normal to and intersecting a center of the applanation surface and an emitter and a detector port respectively inputting and outputting light that is internally reflected within the prism:
  a. wherein the emitter and detector ports are arranged opposite each other on opposite sides of the longitudinal axis and are angled about 45° to the longitudinal axis so that light transmitting surfaces of the emitter and detector ports are about perpendicular to each other;
  b. wherein the prism has an emitter and a detector reflecting surface that are arranged opposite to each other on opposite sides of the longitudinal axis and proximate to the applanation surface, and the emitter and detector reflecting surfaces are respectively opposite the emitter and detector ports and are approximately parallel to each other
  c. the emitter and emitter port being arranged so that a light path from the emitter port is angled about 45° to the longitudinal axis and directed across the longitudinal axis for incidence upon the emitter reflecting surface; and
  d. the detector and detector port being arranged so that a light path to the detector port for light reflected from the applanation surface leads from the detector reflicting surface at an angle of about 45° to the longitudinal axis to cross the longitudinal axis and be output at the detector port.

20. The improvement of claim 19 wherein the prism has a surface normal to the longitudinal axis opposite the applanation surface.

21. The improvement of claim 19 wherein the applanation surface is circular with a diameter of about 7 millimeters.

22. The improvement of claim 19 wherein the emitter and detector ports respectively engage the emitter and the detector when the prism is positioned for operation within tonometer.

23. The improvement of claim 19 wherein the light path from the emitter and the light path to the detector are never nearly parallel within the prism.

24. The improvement of claim 19 further comprising a prism holder configured to receive and retain the prism during operation and the emitter and detector are arranged in the prism holder in respective communication with the emitter and detector ports.

25. The improvement of claim 24 wherein the prism is removable from and replaceable into the holder.

26. The improvement of claim 24 wherein the emitter and detector ports respectively contact the emitter and the detector.

27. An applanation tonometer having an applanation prism with an applanation surface that engages a cornea of an eye being examined, an optical system including an emitter directing light into the prism to be incident on and at least partially reflected from the applanation surface and a detector detecting light reflected from the applanation surface, and a microprocessor responsive to a signal from the detector representing total light reflected from the applanation surface and received by the detector, the tonometer further comprising:
 a. a receiver for input to the microprocessor of a value representing corneal thickness of the eye being examined for intraocular pressure; and
 b. the microprocessor being programmed to adjust an intraocular pressure measurement to accommodate for the corneal thickness value received via input to the receiver.

28. An applanation tonometer having an applanation prism with an applanation surface that engages a cornea of an eye being examined, an optical system including an emitter directing light into the prism to be incident on and at least partially reflected from the applanation surface and a detector detecting light reflected from the applanation surface, and a microprocessor responsive to a signal from the detector representing total light reflected from the applanation surface and received by the detector wherein the microprocessor is programmed to calibrate the tonometer by establishing a detector offset value for full emitter illumination and full reflection from the applanation surface and establishing a slope value applied to a detected measurement value, the slope value being a predetermined detector output value departing from the offset value divided by an emitter-energizing value needed to produce the predetermined detector output value.

29. An applanation tonometer having an applanation prism with an applanation surface that engages a cornea of an eye being examined, an optical system including an emitter directing light into the prism to be incident on and at least partially reflected from the applanation surface and a detector detecting light reflected from the applanation surface, and a microprocessor responsive to a signal from the detector representing total light reflected from the applanation surface and received by the detector, the tonometer further comprising:
 a. the prism being removable from the tonometer and a replaced prism being insertable into the tonometer;
 b. the tonometer having a replaced prism detector arranged for sensing the presence of the replaced prism within the tonometer and sending a signal to the microprocessor that the replaced prism has been inserted into the tonometer in place of a removed prism;
 c. the microprocessor being programmed to respond to the signal from the replaced prism detector for permitting only a predetermined number of intraocular pressure measurement sequences; and
 d. interaction between the prism, the replaced prism detector, and the microprocessor being arranged to require replacement of the prism after the predetermined number of intraocular pressure measurements before permitting a new sequence of intraocular pressure measurements.

30. An applanation tonometer having an applanation prism with an applanation surface that engages a cornea of an eye being examined, an optical system including an emitter directing light into the prism to be incident on and at least partially reflected from the applanation surface and a detector detecting light reflected from the applanation surface, and a microprocessor responsive to a signal from the detector representing total light reflected from the applanation surface and received by the detector, the tonometer further comprising:
 a. a receiver for input to the microprocessor of a value representing corneal curvature of the eye being examined for intraocular pressure; and
 b. the microprocessor being programmed to adjust an intraocular pressure measurement to accommodate for the corneal curvature value received via input to the receiver.

* * * * *